(12) United States Patent
Jones et al.

(10) Patent No.: US 6,881,581 B2  
(45) Date of Patent: Apr. 19, 2005

(54) HIGH-DENSITY LIPOPROTEIN ASSAY DEVICE AND METHOD

(75) Inventors: Ronald M. Jones, Mountain View, CA (US); Thomas E. Worthy, Walnut Creek, CA (US); Anthony J. Nugent, Dublin, CA (US)

(73) Assignee: Cholestech Corporation, Hayward, CA (US)

( * ) Notice: Subject to any disclaimer, the term of this patent is extended or adjusted under 35 U.S.C. 154(b) by 268 days.

(21) Appl. No.: 10/346,685

(22) Filed: Jan. 17, 2003

(65) Prior Publication Data

US 2003/0166291 A1 Sep. 4, 2003

Related U.S. Application Data

(60) Provisional application No. 60/349,926, filed on Jan. 18, 2002.

(51) Int. Cl.[7] ................................................ G01N 33/49
(52) U.S. Cl. .................. 436/71; 436/169; 436/170; 436/175; 436/177; 436/178; 422/56; 422/58
(58) Field of Search ..................... 436/71, 169, 170, 436/175, 177, 178; 422/56, 58

(56) References Cited

U.S. PATENT DOCUMENTS

| | | | |
|---|---|---|---|
| 4,623,628 A | | 11/1986 | Maaskant et al. |
| 4,814,077 A | | 3/1989 | Furuyoshi et al. |
| 4,959,324 A | | 9/1990 | Ramel et al. |
| 4,999,287 A | | 3/1991 | Allen et al. |
| 5,087,556 A | * | 2/1992 | Ertinghausen ............... 435/7.9 |
| 5,114,350 A | | 5/1992 | Hewett |
| 5,135,716 A | | 8/1992 | Thakore |
| 5,213,964 A | | 5/1993 | Jones |
| 5,213,965 A | | 5/1993 | Jones |
| 5,215,886 A | | 6/1993 | Patel et al. |
| 5,401,466 A | * | 3/1995 | Foltz et al. ................... 422/56 |
| 5,417,863 A | | 5/1995 | Varady et al. |
| 5,426,030 A | | 6/1995 | Rittersdorf et al. |
| 5,496,637 A | | 3/1996 | Parham et al. |
| 5,543,054 A | | 8/1996 | Charkoudian et al. |
| 5,580,743 A | * | 12/1996 | Rittersdorf et al. ........... 435/11 |
| 5,786,164 A | * | 7/1998 | Rittersdorf et al. ........... 435/11 |
| 6,156,492 A | | 12/2000 | Kobayashi et al. |
| 2003/0175153 A1 | * | 9/2003 | Anaokar et al. ............... 422/56 |
| 2004/0023400 A1 | * | 2/2004 | Tamura et al. ................ 436/71 |

FOREIGN PATENT DOCUMENTS

| | | |
|---|---|---|
| EP | 1 029 928 A2 | 1/2000 |
| WO | WO 99/58966 A1 | 11/1999 |
| WO | WO 02/02796 A2 | 1/2002 |

OTHER PUBLICATIONS

Copy of International Search Report for International Application No. PCT/US03/01354.

* cited by examiner

*Primary Examiner*—Jeffrey R. Snay  
(74) *Attorney, Agent, or Firm*—LeeAnn Gorthey; Perkins Coie LLP

(57) ABSTRACT

An assay device and method for measuring the concentration of HDL-associated cholesterol in a blood-fluid sample are described. The assay design is such that removal of non-HDL lipoproteins from a sample and assay of HDL cholesterol in the sample occur without interruption of the assay. The device also prevents interference by reagents used for the HDL assay with other assays carried out on the same sample.

28 Claims, 3 Drawing Sheets

HIGH-DENSITY LIPOPROTEIN ASSAY DEVICE AND METHOD

This application claims the benefit of U.S. Provisional Application No. 60/349,926, filed Jan. 18, 2002, which is incorporated herein by reference in its entirety.

FIELD OF THE INVENTION

The present invention relates to a method of determining the concentration of high density lipoprotein (HDL)-associated cholesterol in a blood-fluid sample, and a diagnostic assay device for carrying out the method.

BACKGROUND OF THE INVENTION

The amount of cholesterol present in the blood is known to be related to the risk of coronary artery disease. Cholesterol circulates in the blood predominantly in protein-bound form. The proteins which transport cholesterol are the lipoproteins, which are subdivided into three classes based on their density. The very-low density lipoproteins (VLDL) are triglyceride-rich lipoproteins which are synthesized in the liver and ultimately converted to low-density lipoproteins (LDL), which transport most of the plasma cholesterol in humans. The high-density lipoproteins (HDL) are lipoproteins which are involved in the catabolism of triglyceride-rich lipoproteins, and in the removal of cholesterol from peripheral tissues and transport to the liver. An inverse relationship between serum HDL levels and risk of coronary disease has been established. In particular, if the proportion of serum cholesterol associated with HDL is low, the risk of coronary disease is increased.

In view of the importance of relative serum cholesterol levels in risk assessment and management of atherogenic disease, considerable effort has been spent screening large populations of both normal and high-risk individuals for serum levels of HDL, LDL, as well as total cholesterol and triglycerides. The effectiveness of treatments of high-risk individuals has been monitored by regular testing of serum levels of cholesterol in the various lipoprotein compartments.

One method for specific HDL cholesterol testing is based on the selective precipitation of non-HDL lipoproteins in serum by polyanionic compounds, such as dextran sulfate, heparin, and phosphotungstate, in the presence of a group-II cation, such as $Mg^{2+}$, $Mn^{2+}$, and $Ca^{2+}$. The specificity and degree of precipitation are dependent on a variety of factors, including the type and concentration of the polyanion/metal agent. In general, the order of precipitation of serum cholesterol particles, with increasing concentration of polyanion, is VLDL, LDL, and HDL. HDL usually remains soluble at concentrations of heparin or dextran sulfate which completely precipitate lower density particles, although minor apoE species of HDL may be co-precipitated with lower density particles. By selective precipitation of lower density particles, HDL serum cholesterol levels can be determined.

In a typical lipid assay procedure, a small volume of blood is drawn and centrifuged to produce a clear plasma or serum sample fluid. The sample fluid is then aliquoted into several assay tubes, for determination of (a) total serum cholesterol, (b) triglycerides, and (c) HDL cholesterol. The HDL sample is precipitated, as above, and the lower density particles are removed by filtration or centrifugation prior to cholesterol detection. The samples are then reacted with an enzyme mix containing cholesterol esterase, cholesterol oxidase, peroxidase and a dye which can be oxidized to a distinctly colored product in the presence of $H_2O_2$. The tubes may be read spectrophotometrically, and the desired total, HDL and LDL cholesterol values determined.

Despite the accuracy and reliability which can be achieved with the liquid-phase cholesterol assay just described, the assay has a number of limitations for use in widespread screening. First, the method uses a venous blood sample, requiring a trained technician to draw and fractionate the blood sample, and aliquot the treated blood to individual assay tubes. At least one of the sample tubes (for HDL determination) must be treated with a precipitating agent, and further processed to remove precipitated material. Although some of these procedures can be automated, analytical machines designed for this purpose are expensive and not widely available outside of large hospitals.

Co-owned U.S. Pat. Nos. 5,213,964, 5,213,965, 5,316,196 and 5,451,370, each of which is incorporated herein by reference, disclose methods and assay devices which substantially overcome many of the above-mentioned problems associated with liquid-assay procedures for measuring serum cholesterol levels. In one embodiment, the device is designed for measuring the concentration of HDL-associated cholesterol in a blood sample also containing LDL and VLDL particles. The device includes a sieving matrix capable of separating soluble and precipitated lipoproteins as a fluid sample migrates through the matrix. A reservoir associated with the matrix is designed to release a precipitating agent, for selectively precipitating LDL and VLDL, as fluid sample is drawn into and through the matrix. This allows HDL separation from the precipitated lipoproteins, based on faster HDL migration through the sieving matrix. The fluid sample, thus depleted of non-HDL lipoproteins, then migrates to a test surface where it is assayed for cholesterol.

It was found that treatment of blood with reagents used in selectively precipitating non-HDL blood lipoproteins resulted in binding of a proportion of the HDL present in the sample to non-coated glass fibers, and that such binding of HDL to the glass fibers during filtering or transport often resulted in spuriously low HDL cholesterol values. This problem was addressed, in co-owned U.S. Pat. No. 5,451,370, by coating the glass fibers in the matrix used for precipitation/sieving and transport of the filtered sample with a hydrophilic polymer or silylating reagent.

In addition to the necessity for such coating to minimize HDL loss, the above-referenced devices also present the possibility of contamination of the flow transport path with the precipitating reagents. Such reagents could interfere with other assay chemistry taking place on other regions of the multi-assay device. The present invention addresses and overcomes these problems.

Further methods and devices for measuring HDL cholesterol in blood samples are disclosed in EP 0408223 and EP 0415298 (Rittersdorf et al.), which describe a continuous assay method carried out on a test strip comprising the following steps and corresponding elements.

The blood sample is applied to a separation layer for separating cellular blood constituents. Driven by capillary forces or gravity, the sample flows through a further carrier containing soluble precipitating agents, which, after dissolving in the serum sample, precipitate non-HDL lipoproteins contained in the sample.

In a further carrier, the precipitated constituents, above, are filtered from the serum sample to prevent their interference with later HDL quantification. In the same carrier, the sample is transported to a position adjacent the HDL-quantification carrier, and is stored until the HDL-quantification step is to be started. Finally, the sample is transferred to an HDL-quantification layer, where HDL cholesterol in the serum sample is quantified by an enzymatic reaction.

A disadvantage of this assay design, which can affect the accuracy of HDL quantification, is that the carrier functioning as a reservoir allows migration of the precipitated constituents into the sample, which interfere with HDL quantification. In addition, during the storage of the serum sample, HDL can be trapped by adhering to the carrier fibers, precipitating reagents can cause further undesired reactions, and the carrier can become clogged by the drying serum sample.

U.S. Pat. No. 5,135,716 (Thakore) discloses additional devices and methods for HDL quantification in a blood fluid sample. In these devices, the fluid sample flows continuously, though an unbroken path, from an inlet well to a carrier for HDL quantification. Accordingly, the ability to control sample volume entering the HDL test carrier, and to control environmental conditions for the HDL assay, is limited. Nor do the devices provide for simultaneous assay of various analytes from a single fluid sample.

It is therefore the object of the present invention to provide a HDL assay device and method which overcome the above-noted prior art disadvantages.

SUMMARY OF THE INVENTION

In one aspect, the invention provides an assay device for measuring serum cholesterol associated with high-density lipoproteins (HDL) in a blood fluid sample also containing low density lipoproteins (LDL) and/or very low density lipoproteins (VLDL), the device comprising:

a sample distribution matrix effective to distribute a blood fluid sample from a sample application region within the matrix to one or more sample collection regions within the matrix;

an HDL assay element, in which HDL concentration can be assayed, spaced apart from the sample distribution matrix, a reagent pad, disposed between the HDL assay element and the sample distribution matrix, and spaced apart from the matrix, the reagent pad containing a reagent effective to selectively remove non-HDL lipoproteins from the fluid sample, and mounting means effective (a) to maintain the device in a sample-distribution position, wherein the HDL assay element and reagent pad are spaced apart from the matrix, and (b) to transfer the device to a test position, whereby the HDL assay element is placed or maintained in contact with the reagent pad, and the reagent pad is, concurrent with or subsequent to the contact, brought into contact with the matrix. In a preferred embodiment, the mounting means is further effective to (c) transfer the device from the test position to a position in which the HDL assay element and reagent pad are spaced apart from the matrix.

Preferably, a lower surface of the HDL assay element is attached to an upper surface of the reagent pad, so that the two are in permanent contact.

In one embodiment, the device further comprises a cassette body to which the sample distribution matrix is attached, and a reaction bar to which the HDL assay element is attached. The mounting means is effective to attach the reaction bar to the cassette body, and to adjust the relative positions of the reaction bar and cassette body between the sample-distribution position and the test position, as described above. Typically, the cassette body further comprises a well for containing the blood fluid sample and a sieving pad for removing cellular blood components from the blood fluid sample, in fluid communication with the sample application region, such that fluid passes from the well through the sieving pad and to the sample matrix.

The HDL assay element typically contains reagents which, in the presence of HDL cholesterol, produce a change in the assay element which can be detected optically. For use in conducting simultaneous assays of multiple analytes on a single sample, the device preferably includes additional assay elements attached to the reaction bar, such that these elements are brought into contact with the sample collection regions when the device is transferred to the testing position. Preferably, the reaction bar is optically transparent, or it includes windows through which the assay elements are visible.

In another embodiment, the HDL assay element comprises a biosensor. Preferably, the biosensor is effective to electrochemically measure production of oxygen or hydrogen peroxide, which is in turn dependent on HDL-associated cholesterol concentration within the sample fluid. Additional assay elements may also comprise biosensors, effective to electrochemically measure production of oxygen or hydrogen peroxide, which is in turn dependent on analyte concentration within the sample fluid.

In another aspect, the invention provides a related method of measuring serum cholesterol associated with high-density lipoproteins (HDL) in a blood fluid sample also containing low density lipoproteins (LDL) and/or very low density lipoproteins (VLDL). The method includes the following operations:

(a) contacting the sample with an absorptive sample distribution matrix through which the sample is distributed to one or more sample collection sites;

(b) bringing into contact with such a sample collection site, a first surface of a reagent pad, to which sample fluid is transferred, containing a reagent effective to selectively remove non-HDL lipoproteins from the fluid, wherein an opposite surface of the reagent pad is in simultaneous contact with an HDL assay element, containing assay reagents effective to produce an indication of HDL cholesterol concentration, such that successive sample volumes proceed from the reagent pad to the HDL assay element, and (c) determining the level of HDL cholesterol in the sample by detection at the HDL assay element.

The blood fluid sample is generally filtered, e.g. via a sieving matrix upstream of the sample distribution matrix, to remove cellular blood components. Step (b) above comprises adjusting the device from a sample-distribution position to a test position, as described above. Preferably, the method also includes the step of breaking the contact between the sample collection site and the first surface of the reagent pad, when a desired amount of sample fluid has been transferred. Fluid contact is thus selectively establishable between the sample matrix and the reagent pad which is connected to the HDL assay element. By the above measures, effective sample distribution and volume control is realized, and sample overload of the corresponding pads/test elements is prevented.

The reagent effective to selectively remove non-HDL lipoproteins from the fluid sample, by binding or precipitation, may include, for example, a sulfonated polysaccharide, such as dextran sulfate. In one embodiment, the reagent pad is impregnated with the reagent in a form which is soluble in the fluid sample, and is of a material effective to entrap precipitated non-HDL lipoproteins within the reagent pad. In another embodiment, the reagent is immobilized to the reagent pad, and non-HDL lipoproteins are removed from the sample by binding to the immobilized reagent.

In a preferred embodiment, the reagent pad comprises a porous polymeric membrane. The membrane may be an asymmetric polymeric membrane, having a smaller pored surface and an opposite, larger pored surface. In this case, it is preferably oriented such that its smaller pored surface faces the HDL assay element.

The HDL assay element may also be a porous polymeric membrane, such as an asymmetric polymeric membrane, preferably oriented such that its larger pored surface faces the reagent pad. In one embodiment, each of the HDL assay element and the reagent pad is an asymmetric polymeric membrane, and the membranes are laminated such that the smaller pored surface of the reagent pad contacts a larger pored surface of the HDL assay element.

In another embodiment, the HDL assay element and/or other assay elements comprise a biosensor, as described above.

The invention provides several advantages over the prior art described above. For example, when the reagent pad containing the precipitating or binding reagent contacts the sample fluid, it is in direct contact with the HDL assay element, thus limiting the temporal contact of the blood sample with these reagents prior to the HDL assay reaction.

If desired, the test method can also be adapted to meet required environmental conditions. Accordingly, the assay can be stopped for a desired time after the sample application and removal of cellular components, but prior to contact with binding or precipitation reagents, e.g. to adjust the surrounding atmosphere or adapt the environmental temperature to support the testing. This is accomplished by maintaining the device in the sample-distribution position. To this end, the sample distribution matrix is designed to additionally serve as a reservoir, if needed.

In the present method, the sample preparation and the HDL evaluation are carried out in separate steps. Sample preparation includes, for example, filtering of cellular blood components and, optionally, temporary storage of the blood sample and adaptation of the blood sample to such test requirements or conditions as temperature, pressure and environmental atmosphere. The HDL evaluation step comprises a time-effective removal of non-HDL constituents and a reliable HDL quantification. By this measure, the temporal contact of the blood sample with the different reagents is reduced, and any chemical interference with the HDL evaluation is prevented. Further, the blood sample is not extensively stored in a small pored carrier, since the HDL evaluation step is executed in a short period.

These and other objects and features of the invention will become more fully apparent when the following detailed description of the invention is read in conjunction with the accompanying drawings.

DETAILED DESCRIPTION OF THE INVENTION

I. Definitions

The terms below have the following meanings unless indicated otherwise.

An element is in "fluid communication" with another element when a fluid is able to travel from one element to the other via capillary action and/or gravity. The elements may be in direct contact, but do not need to be in direct contact; i.e., other elements through which said fluid can pass may be intervening. An element is "not in fluid communication" with another element when a fluid is not able to travel from one element to the other via capillary action and/or gravity. Typically, the elements are physically separated, i.e. spaced apart.

A "pad", such as a reagent pad or assay pad, as used herein, may comprise any material, such as a porous membrane or fibrous strip, which can contain impregnated or immobilized reagents and through which fluid can move via capillary action and/or gravity.

II. Assay Device

Figure 1:
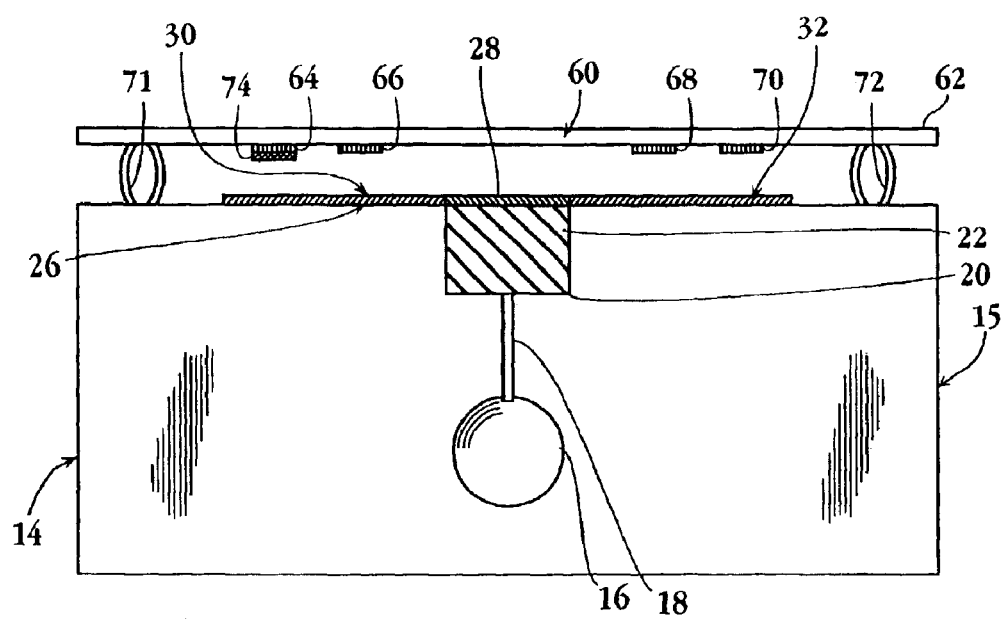
FIG. 1 is a side view of a multi-analyte assay device constructed in accordance with one embodiment of the invention.
Figure 2:
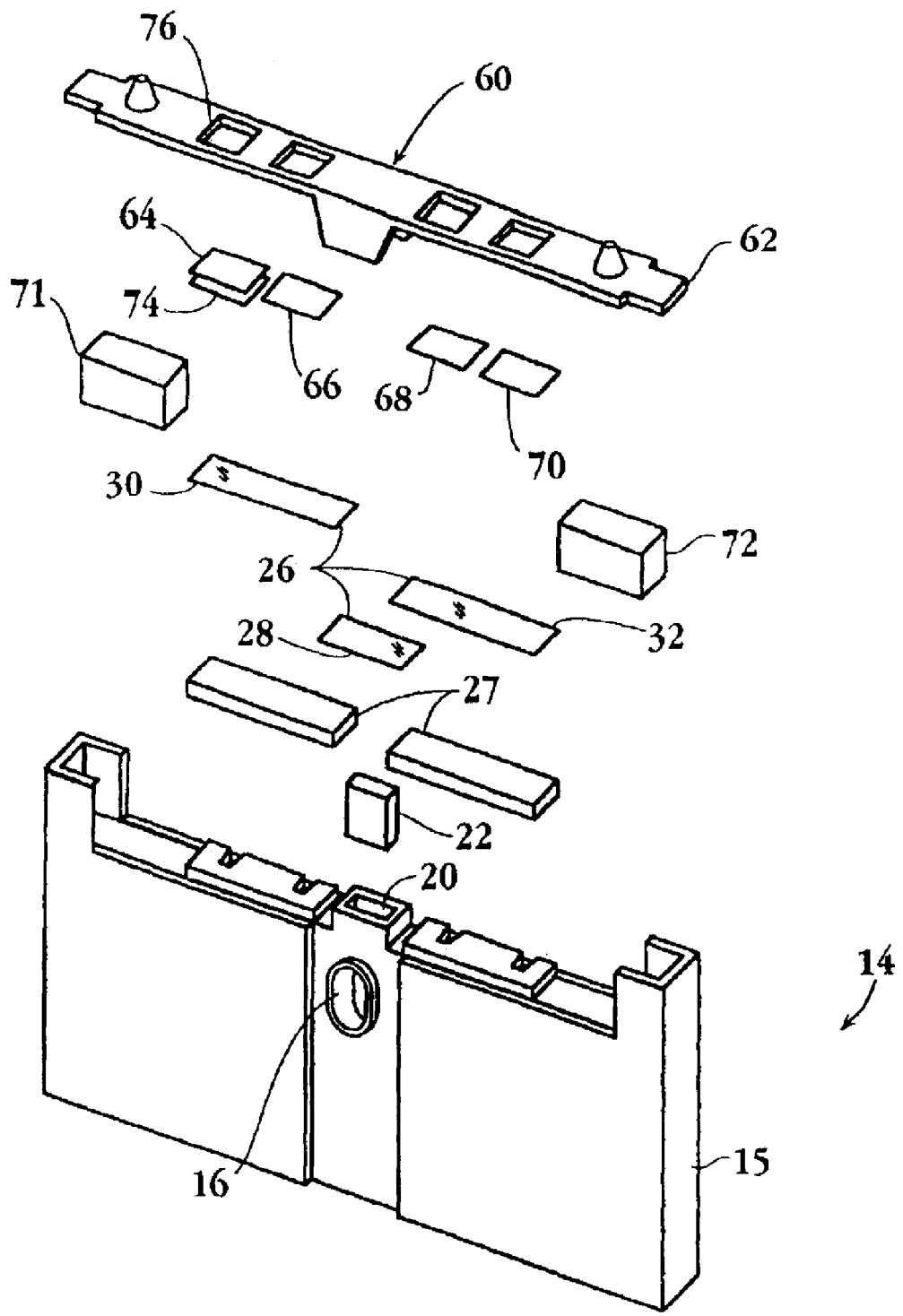
FIG. 2 is a perspective view, in exploded form, of a multi-analyte assay device constructed in accordance with one embodiment of the invention.

FIGS. 1 and 2 illustrate two embodiments of a multiple-analyte assay device 14 constructed in accordance with the present invention, with FIG. 2 shown in exploded format. The device is designed particularly for determining serum cholesterol associated with HDL (also referred to as HDL-associated cholesterol or simply HDL cholesterol) using a small volume of blood sample, typically between 10–50 $\mu$l of blood. Other assays, such as total cholesterol or triglyceride level, can be determined simultaneously from the same sample. Determination of HDL-associated cholesterol may also be referred to simply as determination of HDL or an HDL assay.

The apparatus includes a main body or support 15 which defines a well 16 dimensioned and sized to receive a quantity of a blood sample, typically between about 25–50 $\mu$l. The well is in fluid contact with a sieving pad 22, which may be carried in a notched region 20 formed in the upper edge of the support. The fluid contact may be direct, or as in the device shown in FIG. 1, provided by a capillary conduit 18 formed in the plate at the base of the well. The support is preferably a plastic plate, with the well, notched region and/or capillary formed by standard molding or machining methods.

Sieving pad 22 carried in region 20 functions to partially remove large particulate matter (including blood cells) as the sample migrates through the pad matrix in a bottom-to-top direction as shown in the figure. Pad 22 is preferably formed of a glass fibrous matrix of material designed to draw aqueous fluid by surface wetting, and to retard the movement of blood cells as the blood sample is drawn through the matrix. That is, the pad serves as a chromatographic medium for separating cell-size particles from soluble serum components on the basis of different migration rates through the medium. One exemplary pad is a glass fiber filter, such as a GF/D or PD008 filter supplied by Whatman, having a packing density of about 0.16 g/cm$^3$. The pad is cut to side dimensions of about 3×8 mm, and a thickness of about 1 mm. The pad is dimensioned to absorb a defined volume of sample fluid, preferably between about 15–25 $\mu$l. Sieving pad 22 may additionally contain red blood cell capture reagents, such as lectins, antibodies specific for red blood cell surface membrane proteins, thrombin, or ion exchange agents.

The sieving pad, 22, in turn, contacts an elongate strip or sample distribution matrix 26 which extends along the upper edge of plate 15. This strip may also be supported by foam cushions 27 or other supports, as shown in FIG. 2. Matrix 26 serves to distribute sample fluid from a central sample-application region 28 of the strip, which is in fluid contact with pad 22, to opposite sample-collection regions 30, 32 adjacent the ends of the matrix. The matrix is preferably formed of glass fibers. The packing density and thickness of the matrix are such as to absorb and distribute volumes of sample fluid, e.g., 10–25 µl, supplied to the sample-application region of the strip to the sample-collection regions of the strip. The matrix has a preferred packing density between about 0.16 g/cm$^3$ and 4.0 g/cm$^3$. One exemplary strip material is a F-165-25A glass fiber filter available from Whatman, having a packing density of about 0.2 gm/cm$^3$ and a thickness of about 0.12 mm.

Because the sample does not contact the glass fibers used for the sieving pad and sample distribution matrix in the presence of precipitation or binding reagent, coating as described in U.S. Pat. No. 5,451,370, is not required to prevent adhesion of HDL. However, if desired, the glass fibers may be coated, e.g. with 5% polyvinyl alcohol by weight.

Device 14 also includes a reaction bar 60 composed of an elongate support 62, and multiple wettable assay elements 64, 66, 68 and 70, carried on the lower surface of the support, at the positions shown. Support 62 preferably is transparent or has windows, e.g. window 76 (FIG. 2), which may simply be openings in the support, which allow the pads to be viewed through the support. The assay elements in the reaction bar can be attached to the support by a transparent or translucent adhesive material, or by sonic welding or other suitable bonding method. Each pad used in a particular assay contains analyte-dependent reagents effective to produce an analyte-dependent change in the pad which can be detected optically, either visually or by a detector, or via a biosensor, as described further below. All or any integral subset of the pads may be employed in a particular assay.

Desirably, the assay elements are porous polymer membranes, preferably having a thickness of about 100–150 µm and side dimensions of about 3 mm. The absorption volume of each element is preferably between about 0.5–1.0 µl. In one embodiment, the assay elements, and in particular that used for HDL assay, are asymmetric membranes; that is, membranes having a porosity gradient across the thickness of the membrane, as described further below. The assay elements may also comprise a biosensor, as described below.

The reaction bar is mounted on support 15 by mounting means effective to (a) maintain the device in a sample-distribution position, wherein the assay elements and reagent pads are spaced apart from the matrix, and to (b) transfer the device to a test position, where the HDL assay element is placed (or maintained, if the two pads are attached together) in contact with the reagent pad, and the reagent pad is, concurrently or subsequently, brought into contact with matrix 26 at a sample collection site. The mounting means can also be used to break such contact after a desired amount of sample has entered the assay elements, and/or after a determined contact time, by transferring the device from the test position to a position in which the assay elements and reagent pads are spaced apart from the matrix (which may be the same as the "sample-distribution" position). Such transferring can be controlled by monitoring the reflectance at the top surface of the assay element, which reflects extent of wetting, as described in co-owned U.S. Pat. No. 5,114,350. Alternatively, when the absorption capacity and rate of sample uptake of the wettable materials are known, the quantity of sample can be controlled with sufficient accuracy simply by using a predetermined contact time.

The mounting means can include, for example, a pair of resilient members, such as elastomeric blocks 71, 72, which act to bias the pads toward a non-transfer or sample-distribution position, at which the pads are spaced apart from the sample distribution matrix, with a spacing typically of between about 0.5 to 1.0 mm. By compression or release of the resilient members, contact between sample distribution matrix 26 and reagent pad 74 and HDL assay element 64 can be selectively established and separated. The support blocks could be compressed by means of springs or a piston-like action. Alternatively, external mechanical devices could engage the main body 15 and/or support 62 and move one towards the other. Such devices may include conventional components such as clamps, pistons, stepper motors, worm gears, or the like. An exemplary system is the Cholestech LDX® Analyzer, a self-contained, automated analyzer advantageous for use with assay devices such as described herein.

In a preferred embodiment, at least one of the assay elements, used for assaying HDL, has affixed thereto a reagent pad 74, as shown in the Figures. Alternatively, such a reagent pad 74 may be supported in a substantially coplanar position between the HDL assay element, with which it may or may not be in contact, and a sample collection region of matrix 26. For example, a compressible support element could support the reagent pad above the matrix, such that movement of the reaction bar towards the main body (or vice versa) would first bring assay element 64 into contact with the upper surface of reagent pad 74, and would then bring the lower surface of the reagent pad into contact with the sample distribution matrix. The reagent pad preferably has a thickness of about 100–150 µm, side dimensions of about 3 mm, and an absorption volume of about 0.5–1.0 µl.

Reagent pad 74, preferably in contact with a selected assay element used for HDL measurement, such as assay element 64 in the drawings, contains a reagent used to selectively remove LDL and VLDL particles from the fluid sample. Such reagents are known in the art as precipitating reagents; see e.g. a review by P S Bachorik et al., *Methods in Enzymology* 78–100 (1986). They include polyanionic compounds, such as sulfonated polysaccharides, heparin, or phosphotungstate, in the presence of a group-II cation, such as $Mg^{2+}$, $Mn^{2+}$, and $Ca^{2+}$. A preferred reagent is a sulfonated polysaccharide, such as dextran sulfate, having a typical molecular weight of 50,000 to 500,000 daltons, in combination with magnesium acetate or chloride, buffered to maintain neutral pH.

The reagent pad is effective to entrap bound or precipitated non-HDL lipoproteins within the reagent pad and prevent them from entering HDL assay element 64. While a glass fiber filter can be used for such a purpose, such glass fibers should be coated to prevent binding HDL in the presence of the reagents, as described in U.S. Pat. No. 5,451,370, cited above. In a preferred embodiment, reagent pad 74 is composed of a porous polymeric membrane, as described further below.

The reagent pad contains reagents for selective removal of non-HDL lipoproteins, as described above. In one embodiment, a membrane is impregnated with such reagents. For example, a polysulfone asymmetric membrane, as described below, is impregnated with an aqueous solution containing dextran sulfate and a magnesium salt, such as magnesium acetate, and dried. An exemplary procedure for preparing such membranes for incorporation into the device is described in Example 1. In this case, the soluble precipitating reagents are released into the sample solution as it penetrates the membrane.

In another embodiment, the reagents are immobilized to the membrane. Preferably, the negatively charged reagent, e.g. dextran sulfate, is immobilized by electrostatic forces and/or covalently to a membrane having positively charged surface groups. An exemplary material for this purpose is a nylon membrane having surface quaternary ammonium groups, such as the AM080 membrane provided by Cuno Corp. (Meridian, Conn.).

In this case, the membrane acts as an affinity separation medium, such that non-HDL lipoproteins bind to the reagent affixed to the membrane, rather than precipitating, and are thereby separated from the sample fluid.

Other commercial polymeric membranes having a cationic surface include Immobilon-Ny+™ (Millipore Corp., Bedford, Mass.), Zetabind® (also from Cuno Corp.), Gene-Screen® (NEN/DuPont, Boston, Mass.), Hybond N+ (Amersham, Piscataway, N.J.) and Posidyne® (Pall Corp., Glen Cove, N.Y.). U.S. Pat. No. 5,543,054 (Charkoudian et al.) describes a method for covalently binding negatively charged carbohydrates to a membrane having reactive moieties in proximity to positively charged moieties on its surface. The membrane is, for example, a porous polymer, e.g. polytetrafluroethylene, polyvinylidene fluoride, polyester, polyamide, polycarbonate, polypropylene, polymethylmethacrylate, polymethacrylate, polysulfone, or polystyrene, coated with Hercules R-4308™ a polyamido-polyamine epichlorohydrin resin In one embodiment, reagent pad 74 is composed of an asymmetric membrane; that is, a membrane having a pore size gradient across its thickness. An asymmetric membrane is particularly preferred for use with precipitating reagents incorporated into the membrane in soluble form, for optimum entrapment of precipitate. The preparation of asymmetric membranes is described, for example, in U.S. Pat. Nos. 4,629,563, 5,171,445, 5,886,059, 5,536,408, 5,562,826, and 4,774,192; in D. R. Lloyd, "Materials Science of Synthetic Membranes", ACS Symposium 269: 1–21 (1985). They are commercially available in a variety of pore sizes and pore size ratios. Materials of fabrication include polysulfones, polyethersulfones, polyamides, polyether amides, polyurethanes, cellulose acetate, polyvinyl pyrrolidone, polystyrenes and modified polystyrenes, as well as blends, copolymers, and laminar composites. An exemplary asymmetric membrane is a polysulfone or polyethersulfone membrane, such as FILTERITE™ membranes provided by USF Filtration and Separations (San Diego, Calif.). Minimum pore sizes typically range from 0.01 to 1.0 $\mu$m, with maximum/minimum pore size ratios up to 100 or more. Thickness is typically 100–150 $\mu$m.

The asymmetric membrane is preferably oriented with its larger pored surface facing the sample application region; that is, facing downward in FIGS. 1 and 2, and its smaller pored surface facing, and preferably contacting, an assay element, e.g. assay element 64, containing reagents for assaying HDL level, as described further below. This orientation allows free access of sample into the pad through the larger pores, and prevents passage of precipitated material, formed as the solution contacts soluble precipitating agent, through the smaller pores, which are generally 1 $\mu$m or less in diameter. This pore size is also preferred for non-asymmetric membranes.

In one embodiment, reagent pad 74 consists of a single membrane. The invention also contemplates the use of multiple stacked membranes, i.e. up to about six, where at least one and preferably each membrane contains reagents for binding or precipitation of non-HDL lipoproteins, for reagent pad 74. They may contain immobilized reagent, as described above, or they may be impregnated with soluble reagent. In the latter case, asymmetric membranes are preferred, and are preferably oriented such that the smaller pored surface of the uppermost membrane faces assay element 64, and the larger pored surface of the lowest membrane faces the sample application region.

In one embodiment, assay element 64 is also a polymeric membrane, containing reagents for assaying HDL level, and may be an asymmetric membrane as described above. In order to present the more uniform surface for optical scanning and quantitation of assay results, an asymmetric membrane employed for assay element 64 is oriented with its smaller pored surface facing upward, and its larger pored surface facing reagent pad 74.

Alternatively, an asymmetric membrane employed for assay element 64 may be oriented with its larger pored surface facing upward and its smaller pored surface facing reagent pad 74. This orientation is more suitable for assays in which a visual, qualitative reading is to be made from the upper surface.

If desired, HDL assay reagents, such as peroxidase, may be immobilized to the assay element membrane, according to well known methods for enzyme immobilization. (See e.g. U.S. Pat. No. 4,999,287; U.S. Pat. No. 5,419,902; Blum, L. J. et al., *Anal. Lett.* 20(2):317–26 (1987); Kiang, S. W. et al., *Clin. Chem.* 22(8):1378–82(1976); Guilbault, G. G., Ed., *Modern Monographs in Analytical Chemistry, Vol. 2: Analytical Uses of Immobilized Enzymes* (1984); Torchilin, V. P., *Progress in Clinical Biochemistry and Medicine, Vol. 11: Immobilized Enzymes in Medicine* (1991).) In another embodiment, a reagent, such as catalase, which is effective to decompose any generated hydrogen peroxide that might diffuse downward from assay element 64, may be included in reagent pad 74.

Figure 3:
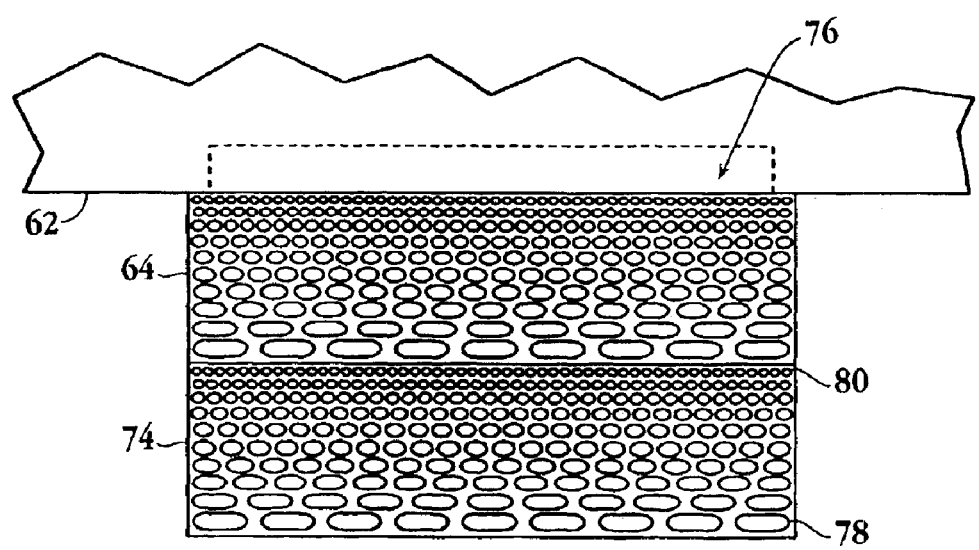
FIG. 3 is a cross section view of two contacting asymmetric membranes, for use as reagent pad and HDL assay element in one embodiment of the invention, in a preferred orientation.

In a preferred embodiment, where two attached polymeric membranes are employed for assay element 64 and reagent pad 74, respectively, the appropriate reagents are impregnated or immobilized, and the membranes are processed as a two-membrane layer for incorporation into the assay device during manufacture. An exemplary two-membrane layer comprising two asymmetric membranes is shown in cross section in FIG. 3, with the preferred orientation shown, with larger pores at 78 and smaller pores at 80.

In a further embodiment, the HDL assay element comprises a biosensor, as described, for example, in PCT Pubn. No. WO 9958966 (Dobson et al.), which is incorporated herein by reference. This document discloses a microscale biosensor device, comprising a conducting surface, a layer of dielectric material overlying the conducting surface, and a plurality of pores extending through the dielectric layer. Each of the pores can act as a microelectrode, converting a chemical response into an electrical signal, by virtue of a biopolymer within the pore in contact with the conducting surface. In use, a fluid containing an analyte to be assayed is applied to the pores so as to be in contact with the biopolymer. In the present HDL assay device, this can be achieved by placing reagent pad 74 in fluid contact with the HDL assay element; that is, the pore-containing surface of the biosensor.

A counter electrode is provided which is in electrical contact with the conducting surface via the sample fluid. A voltage is be applied between the counter electrode and the conducting surface, and the current that flows therebetween is measured. The measured current is indicative of the amount of a chosen analyte in the assayed fluid.

The microelectrodes preferably function as amperometric biosensors. Briefly, an amperometric biosensor functions by the production of a current when a potential is applied between two electrodes. An example is the Clark oxygen electrode, which measures current produced by reduction of oxygen or oxidation of hydrogen peroxide.

The dependence of such biosensors on dissolved oxygen concentration can be overcome by the use of 'mediators', which transfer the electrons directly to the electrode, bypassing the reduction of the oxygen co-substrate. Ferrocenes represent a commonly used family of mediators.

The biopolymer within the microelectrode pores is typically an enzyme, such as, for the measurement of HDL-associated cholesterol, cholesterol oxidase. Cholesterol is oxidized by cholesterol oxidase to the corresponding ketone, liberating hydrogen peroxide, which can then be converted to water and oxygen by the enzyme peroxidase. Either oxygen or hydrogen peroxidase is then measured electrochemically at the biosensor.

III. Assay Method

In operation, a blood sample is placed into well 16, and is imbibed by capillary action through sieving matrix 22, where large particulates, including red blood cells, are removed, and thence into sample distribution matrix 26. These steps take place while the device is in a "sample-distribution" position, such that the sample distribution matrix does not contact the reagent or assay elements. When the serum sample reaches the sample-collection sites, such as sites 30 and 32 adjacent the ends of matrix 26, the device is adjusted to a test position, preferably by moving reaction bar 60, to place assay elements 66, 68, and 70 and reagent pad/assay element 74/64 (in the embodiment shown in the Figures) in contact with the matrix. In this position, sample fluid in the matrix is drawn into each contacted pad by capillary flow, with fluid movement occurring in a direction normal to the pad surfaces. The plate is held at this position until a desired degree of wetting of the pads is achieved. The plate is then moved, if desired, to break contact between the sample distribution matrix and the assay elements and reagent pad(s), when a desired amount of sample fluid has entered the assay elements, and/or after an appropriate contact time, e.g. as described in Example 2 below.

In embodiments of the device in which reagent pad 74 is not affixed to assay element 64, respective movement of the reaction bar and main body toward each other, typically by moving the reaction bar downward, first places assay element 64 in contact with reagent pad 74, to approximate the arrangement of elements shown in the Figures, and further movement then places the reagent pad in contact with the sample distribution matrix. Contact is maintained until a desired degree of wetting is achieved, as described above.

Sample serum entering reagent pad 74 contacts precipitating or binding reagent contained in the membrane, such that non-HDL lipoproteins are selectively precipitated and retained by filtration, in the case of soluble reagent, or bound to the membrane, in the case of immobilized reagent. The membrane is thus effective to entrap non-HDL lipoproteins, while allowing passage of serum containing liquid-phase HDL to HDL assay element 64. The HDL assay element contains reagents for quantification of HDL-associated cholesterol. Preferably, these include cholesterol esterase, for releasing free cholesterol from HDL; cholesterol oxidase, for producing $H_2O_2$ by reaction with free cholesterol; peroxidase, which converts $H_2O_2$ to oxygen and water; and a coupled dye system which is converted, in the presence of peroxidase and $H_2O_2$, to a distinctively colored signal reaction product. Alternatively, the generated oxygen or $H_2O_2$ may be measured by the use of a biosensor, as described above.

During operation, as sample fluid passes through the HDL assay path, comprising pads 74 and 64, its leading edge passes in an upward direction through pad 74, where non-HDL lipoproteins react and are entrapped, and directly to adjacent assay element 64, where HDL reacts with the assay reagents therein, for measurement of HDL-associated cholesterol. Further portions of sample continue to be in contact with pad 74 during this time, and proceed from pad 74 to pad 64 in a like manner, until the absorption capacity is reached. Accordingly, quantification of HDL-associated cholesterol in assay element 64 occurs concurrently with the precipitation or binding reaction taking place in reagent pad 74. Preferably, the volume of sample fluid transferred to the HDL assay path (comprising elements 74 and 64) from the sample distribution matrix is equal to or greater than the absorption capacity of assay element 64, and less than or equal to the combined absorption capacity of assay element 64 and reagent pad 74.

One advantage of the current device and method is that the sample distribution path does not contain non-HDL precipitating or binding reagents; such reagents are present only in reagent pad 74. Therefore, the possibility of interference from these reagents, in assays of analytes other than HDL, is eliminated.

Preferably, each of the assay elements contains reagent components for producing $H_2O_2$ via reaction of the analyte with an enzyme; the $H_2O_2$ subsequently converts a substrate reagent to a colored signal reaction product, or is measured electrochemically, as described above. Such components include, for example, peroxidase and a coupled dye system which is converted by the peroxidase, in the presence of $H_2O_2$, to a distinctively colored signal reaction product. Enzymatic color reactions which employ a variety of substrate-specific oxidases, for enzymatic generation of $H_2O_2$, and subsequent oxidation of a dye to form a colored reaction product, are well known.

A device having four or more reaction pads can be used to simultaneously measure HDL cholesterol (HDL), glucose, total cholesterol (TCh), and triglyceride lipid (TG). Each pad contains the above-described common pathway components (peroxidase and a coupled dye system) such that generated $H_2O_2$ can be measured or produces a distinctly colored signal reaction product. The total cholesterol assay element, which is exposed to serum without exposure to a precipitating or binding reagent, and the HDL assay elements each include, in addition to the common pathway components, cholesterol esterase, for releasing esterified cholesterol in free-cholesterol form from serum lipoproteins, including HDL, LDL, and VLDL particles, and cholesterol oxidase, for producing $H_2O_2$ by reaction with free cholesterol in the sample fluid, as described above. The glucose assay pad includes glucose oxidase, in addition to the common-pathway components. The triglyceride pad includes, in addition to the common-pathway components, lipase, L-glycerol kinase, and L-glycerol-3-phosphate oxidase, for generating $H_2O_2$ from triglyceride, via the intermediate L-glycerol-3-phosphate. The serum sample drawn into the TG pad is not exposed to precipitating or binding reagents, and thus contains all of the serum lipoproteins, so the TG signal represents total serum triglycerides.

Reference standard pads may also be employed; see, for example, the system described in co-owned U.S. Pat. No. 5,114,350, which is incorporated herein by reference.

As noted above, one advantage of the current device and method is that the sample distribution matrix does not contain non-HDL precipitating or binding reagents; such reagents are present only in reagent pad 74. Therefore, the possibility of interference by these reagents, in assays of analytes such as total serum cholesterol and total triglycerides, is eliminated.

EXAMPLES

The following examples are provided to illustrate but not to limit the invention.

Example 1

Preparation of Reagent Membrane with Soluble Precipitant and HDL Test Membrane

To prepare a reagent membrane with soluble precipitant, an aqueous solution containing 1 mg/ml dextran sulfate (500,000 MW) and 12.5 mM $Mg(OAc)_2$ is dispensed onto a polysulfone asymmetric membrane 0.22 inches in width. The membrane thickness is 127+/−5 μm, with a bubble point of 85+/−5 psi. The reagent is dispensed at a rate of 16.6 ul/inch, and the membrane is dried for 20 minutes at 50° C. in a continuous roll process. Lengths of e.g. 100 feet are prepared in this manner and cut to fit the assay devices.

To prepare an HDL reaction membrane, a similar asymmetric polysulfone membrane is impregnated with the following aqueous formulation: cholesterol oxidase 36.5 Units/ml, cholesterol esterase 215 Units/ml, peroxidase 200 Units/ml, 4-aminoantipyrine 1.88 μm/ml, and TOOS (3-[ethyl(3-methylphenyl)amino]-2-hydroxy propanesulfonic acid) 12.05 μm/ml. Dispense rate and drying time are as for the reagent membrane, above.

The two membranes may be attached separately (sequentially) to the reaction bar by ultrasonic welding, or they may be attached simultaneously with a single ultrasonic weld step.

Example 2

Assay Procedure

The following assays were carried out in an LDX® analyzer, using reagent membranes and HDL assay elements prepared essentially as described in Example 1. Sample (35 μl of serum or whole blood) was applied to the sample well and allowed to distribute through the sample distribution matrix for 2 minutes. The reaction bar was then contacted with the matrix for 3 seconds, a time sufficient to transfer enough serum to fill the reagent pad and assay element (combined capacity about 1.5 μl), after which the bar was returned to its original position. Reflectance readings were taken from the upper surface of the HDL assay element every 3 seconds for 150 seconds, to monitor the progress of the HDL assay reaction. The minimum reflectance value attained was then converted to mg/dL of HDL cholesterol according to a previously established calibration curve.

The concentration values below (mg/dL) are from five serum samples analyzed as described above and on a Beckman reference analyzer, showing excellent correlation.

| Sample No. | HDL assay | Beckman reference |
|---|---|---|
| A010904 | 23.8 | 24.5 |
| 10906 | 43.0 | 41.9 |
| 10502 | 61.5 | 59.6 |
| 10801 | 80.6 | 78.7 |
| 10805 | 92.4 | 87.2 |

It is claimed:

1. An assay device for measuring serum cholesterol associated with high-density lipoproteins (HDL) in a blood fluid sample also containing low density lipoproteins (LDL) or very low density lipoproteins (VLDL), the device comprising:
   a sample distribution matrix effective to distribute a blood fluid sample from a sample application region within the matrix to one or more sample collection regions within the matrix;
   an HDL assay element, in which HDL concentration can be assayed, spaced apart from said sample distribution matrix,
   a reagent pad, disposed between said HDL assay element and said sample distribution matrix, and spaced apart from said matrix, said reagent pad containing a reagent effective to selectively remove non-HDL lipoproteins from the fluid sample, and
   mounting means effective (a) to maintain said device in a sample-distribution position, wherein said HDL assay element and reagent pad are spaced apart from said matrix, and (b) to transfer said device to a test position, whereby the HDL assay element is placed or maintained in contact with the reagent pad, and the reagent pad is, concurrent with or subsequent to said contact, brought into contact with said matrix.

2. The device of claim 1, wherein a lower surface of the HDL assay element is attached to an upper surface of the reagent pad.

3. The device of claim 1, further comprising a cassette body to which said sample distribution matrix is attached.

4. The device of claim 3, further comprising a reaction bar to which said HDL assay element is attached.

5. The device of claim 4, wherein said mounting means is effective to attach said reaction bar to said cassette body and to adjust the relative positions of the reaction bar and cassette body between said sample-distribution position and said test position.

6. The device of claim 3, wherein said cassette body further comprises a well for containing said blood fluid sample and a sieving pad for removing cellular blood components from said blood fluid sample, in fluid communication with said sample application region.

7. The device of claim 4, further comprising additional assay elements attached to said reaction bar, such that said pads are brought into contact with said sample collection regions when the device is transferred to the testing position.

8. The device of claim 1, wherein said mounting means is further effective to (c) transfer the device from said test position to a position in which said HDL assay element and reagent pad are spaced apart from said matrix.

9. The device of claim 1, wherein said reaction bar is optically transparent or includes windows through which said assay elements are visible.

10. The device of claim 1, wherein said reagent includes a sulfonated polysaccharide.

11. The device of claim 1, wherein said reagent pad is impregnated with said reagent in a form which is soluble in said fluid sample, and is of a material effective to entrap precipitated non-HDL lipoproteins within the reagent pad.

12. The device of claim 1, wherein said reagent is immobilized to said reagent pad.

13. The device of claim 1, wherein said HDL assay element contains reagents which, in the presence of HDL-associated cholesterol, produce a change in the assay element which can be detected optically.

14. The device of claim 1, wherein said HDL assay element comprises a biosensor.

15. The device of claim 14, wherein said biosensor is effective to measure production of oxygen or hydrogen peroxide which is dependent on HDL-associated cholesterol concentration within said element.

16. The device of claim 1, wherein said reagent pad comprises a porous polymeric membrane.

17. The device of claim 15, wherein said reagent pad is an asymmetric polymeric membrane, having a smaller pored surface and an opposite, larger pored surface.

18. The device of claim 17, wherein said membrane is oriented such that its smaller pored surface faces the HDL assay element.

19. The device of claim 1, wherein each of said HDL assay element and said reagent pad is an asymmetric polymeric membrane, and said membranes are laminated such that the smaller pored surface of the reagent pad contacts a larger pored surface of the HDL assay element.

20. A method of measuring serum cholesterol associated with high-density lipoproteins (HDL) in a blood fluid sample also containing low density lipoproteins (LDL) or very low density lipoproteins (VLDL), comprising (a) contacting the sample with an absorptive sample distribution matrix through which said sample is distributed to one or more sample collection sites;

(b) bringing into contact with such a sample collection site, a first surface of a reagent pad, to which said sample is transferred, containing a reagent effective to selectively remove non-HDL lipoproteins from the fluid sample, wherein an opposite surface of said reagent pad is in simultaneous contact with an HDL assay element, containing assay reagents effective to produce an indication of HDL cholesterol concentration, such that successive sample volumes proceed from said reagent pad to said HDL assay element, and (c) determining the level of HDL cholesterol in said sample by detection at said HDL assay element.

21. The method of claim 20, further comprising the step of breaking said contact between the sample collection site and the first surface of the reagent pad, when a desired amount of sample has been transferred.

22. The method of claim 20, wherein said reagent pad is impregnated with said reagent in a form which is soluble in said fluid sample, and is of a material effective to entrap precipitated non-HDL lipoproteins within the reagent pad.

23. The method of claim 20, wherein said reagent effective to selectively remove non-HDL lipoproteins is immobilized to said reagent pad.

24. The method of claim 22, wherein said reagent pad comprises an asymmetric polymeric membrane, having a smaller pored surface and an opposite, larger pored surface.

25. The method of claim 24, wherein said membrane is oriented such that its smaller pored surface faces said HDL assay element.

26. The method of claim 20, wherein said HDL assay element comprises a biosensor.

27. The method of claim 26, wherein said biosensor is effective to measure production of oxygen or hydrogen peroxide which is dependent on HDL-associated cholesterol concentration within said element.

28. The method of claim 24, wherein each of said HDL assay element and said reagent pad is an asymmetric polymeric membrane, and said membranes are laminated such that the smaller pored surface of the reagent pad contacts a larger pored surface of the HDL assay element.

* * * * *